(12) United States Patent
Weber et al.

(10) Patent No.: US 7,713,223 B2
(45) Date of Patent: May 11, 2010

(54) HAND AND/OR WRIST BRACE APPARATUS

(75) Inventors: James J. Weber, Santa Barbara, CA (US); David Auerbach, Calabasas, CA (US); Shane M. Woods, Fillmore, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 159 days.

(21) Appl. No.: 11/986,065

(22) Filed: Nov. 21, 2007

(65) Prior Publication Data

US 2009/0131843 A1 May 21, 2009

(51) Int. Cl.
- A61F 5/00 (2006.01)
- A61F 13/06 (2006.01)
- A61F 5/37 (2006.01)
- A61L 15/00 (2006.01)
- A61B 19/00 (2006.01)
- A41D 13/08 (2006.01)

(52) U.S. Cl. .................. 602/21; 602/1; 602/5; 602/20; 602/22; 602/30; 602/23; 602/75; 602/62; 128/869; 128/878; 128/879; 128/880; 128/892; 2/16

(58) Field of Classification Search ............... 602/1, 602/5, 20–22, 30, 23, 75, 62; 128/869, 878, 128/879, 880, 892; 2/16
See application file for complete search history.

(56) References Cited

U.S. PATENT DOCUMENTS

| | | | |
|---|---|---|---|
| 5,513,657 A * | 5/1996 | Nelson | 128/879 |
| 5,928,172 A | 7/1999 | Gaylord | |
| 6,702,772 B1 | 3/2004 | Colditz | |
| 7,276,039 B2 | 10/2007 | Garelick et al. | |
| 2009/0018477 A1* | 1/2009 | Brewer | 602/21 |

FOREIGN PATENT DOCUMENTS

WO   WO 01/60289   * 2/2001

* cited by examiner

*Primary Examiner*—Patricia M Bianco
*Assistant Examiner*—Tarla R Patel
(74) *Attorney, Agent, or Firm*—William W. Haefliger

(57) ABSTRACT

Hand and/or wrist support apparatus, comprising in combination, a first brace configured for application to the hand and/or wrist of the user, and a second brace configured for application over at least a portion of the first brace, each brace configured for in-place retention, providing support to a substantial portion of the hand and/or wrist of the user, including the thumb.

17 Claims, 6 Drawing Sheets

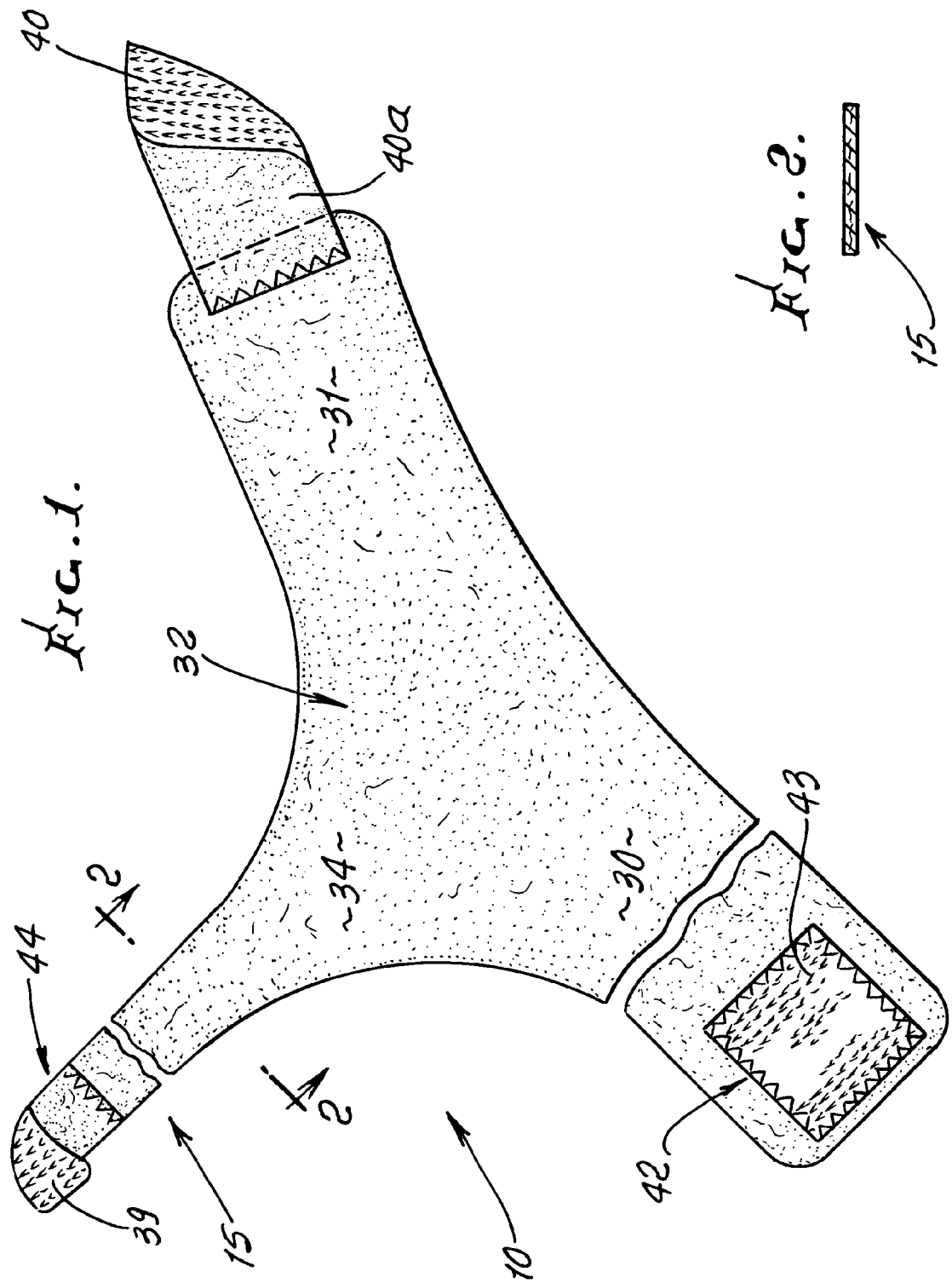

HAND AND/OR WRIST BRACE APPARATUS

BACKGROUND OF THE INVENTION

This invention relates generally to secure bracing of the thumb and/or CMC joint in a selected position.

There is need for simple, effective, easily applied bracing of the thumb and/or CMC joint, and/or wrist, against unwanted movement, and particularly in accordance with the unusual advantages in structure, functions, and results as are now provided by the present invention.

SUMMARY OF THE INVENTION

It is a major object of the present invention to provide method and apparatus meeting the above need. Basically, the hand and/or wrist, and/or thumb bracing apparatus comprises a) a first brace configured for application to the hand and/or wrist of the user, b) and a second brace configured for application over at least a portion of the first brace, c) each brace configured for in-place retention, providing support to a substantial portion of the hand and/or wrist of the user, including the thumb.

Another object is to provide first and second braces as referred to, wherein the second brace is also configured for application to the hand and/or wrist of the user, the first brace configured for application over at least a portion of the second brace. The use of dual cooperating braces as referred to imparts highly secure bracing effect, especially to the thumb, as will appear. Also, the two braces can be used selectively and individually, as well as in tandem, one over the other, as referred to. Such individual usage includes the steps:

d) selecting one of said first and second braces for application to the hand and/or wrist of the user, and e) then applying said one of the braces to the hand and/or wrist of the user.

That one brace typically includes a strap extensible over the web between the user's thumb and forefinger, and tensioning the strap during application of the one brace to the hand and/or wrist of the user. When both braces are applied, one over the other, the user's thumb receives support from each of the applied braces, and to greater extent about the thumb than if only one of the braces is applied.

An added object is to provide both braces with generally annularly extending portions, one configured for application to the wrist of the user, and the other configured for application over the one brace annular portion.

Such portions may comprise wraps extensible about the wrist of the user; and thumb biasing means in the form of a strap or a thumb receiving sleeve, to be tensioned, may be attached to, or attachable to such wraps. Such a strap may be extensible over the web between the user's thumb and forefinger; and if both braces are used, the strap and sleeve may cooperate to exert dual bracing forces on the thumb, with high, in-position, securement effect otherwise not achievable. If lesser securement is desired, either of the two braces (one with strap, the other with thumb sleeve) may be selected and employed.

Another object is to provide a dual brace package, whereby the user can select:

one brace, as with strap, for securement, the other brace, as with thumb sleeve, for securement, both braces applied, the other brace applied over the one brace, for enhanced securement, both braces applied, the one brace applied over the other brace, for enhanced securement effect.

Such securement is with respect to one or both of: the thumb position, and/or the CMC joint position, as for example during arthritis and/or sprain treatment, and thereby achieve maximum bracing comfort during such treatment.

These and other objects and advantages of the invention, as well as the details of an illustrative embodiment, will be more fully understood from the following specification and drawings, in which:

DRAWING DESCRIPTION

FIG. 1 is a plan view of a first brace, in extended, unwrapped condition;

FIG. 2 is a section taken on lines 2-2 of FIG. 1;

DETAILED DESCRIPTION

Figure 3:
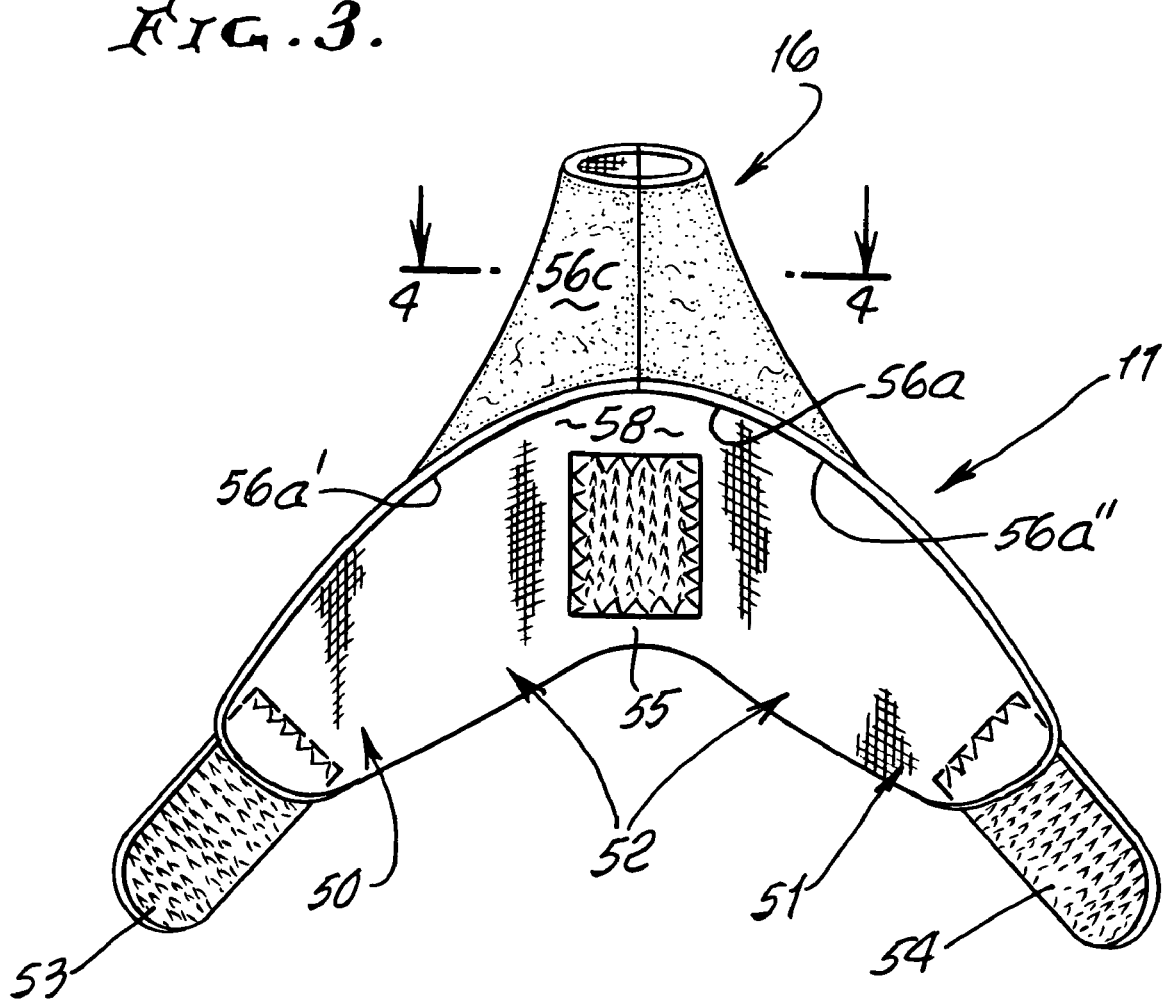
FIG. 3 is a plan view of a second brace in extended, unwrapped condition.
Figure 5:
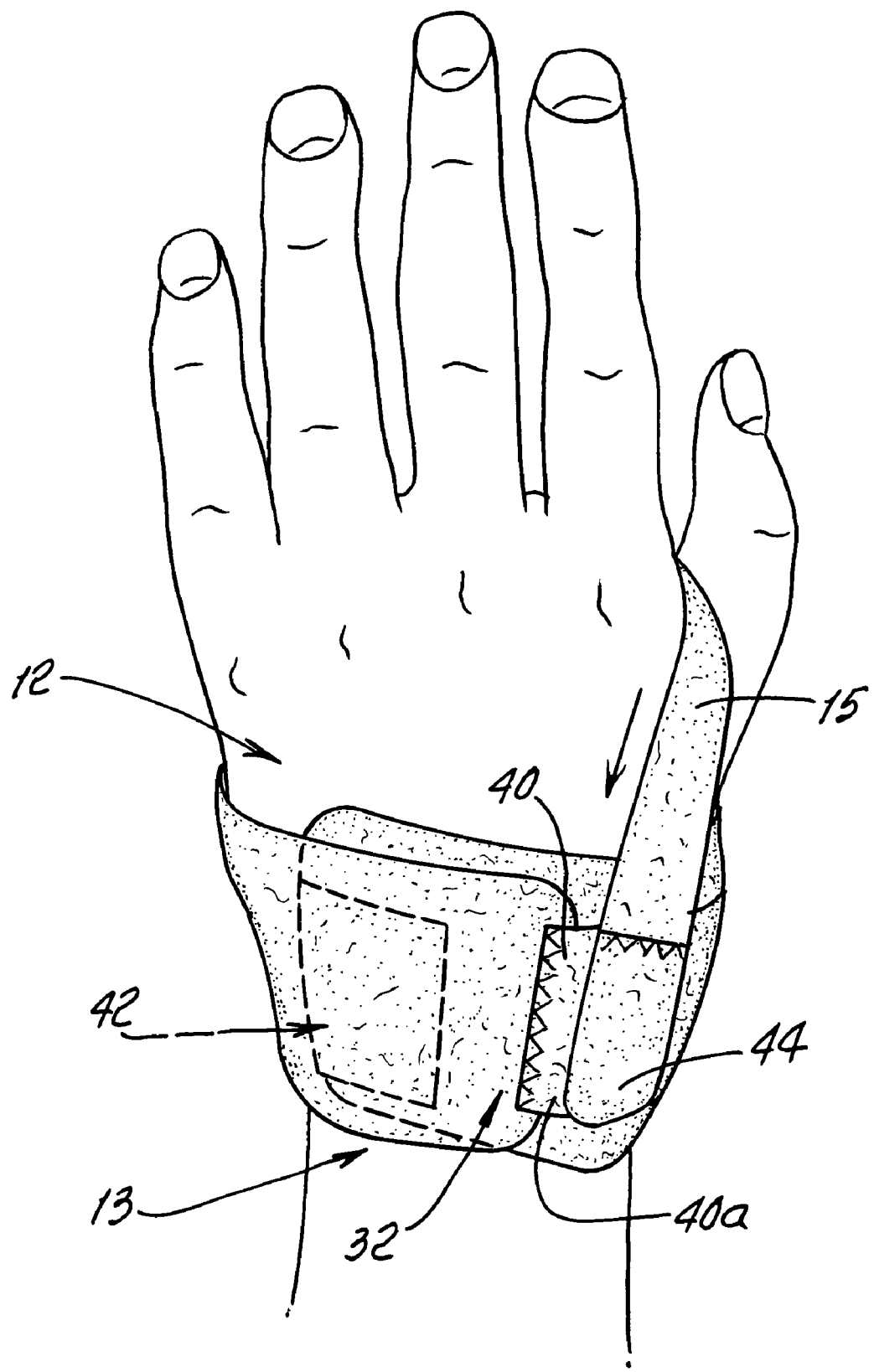
FIG. 5 is a view of a selected one of the braces as applied to the back side of the user's hand and wrist.
Figure 6:
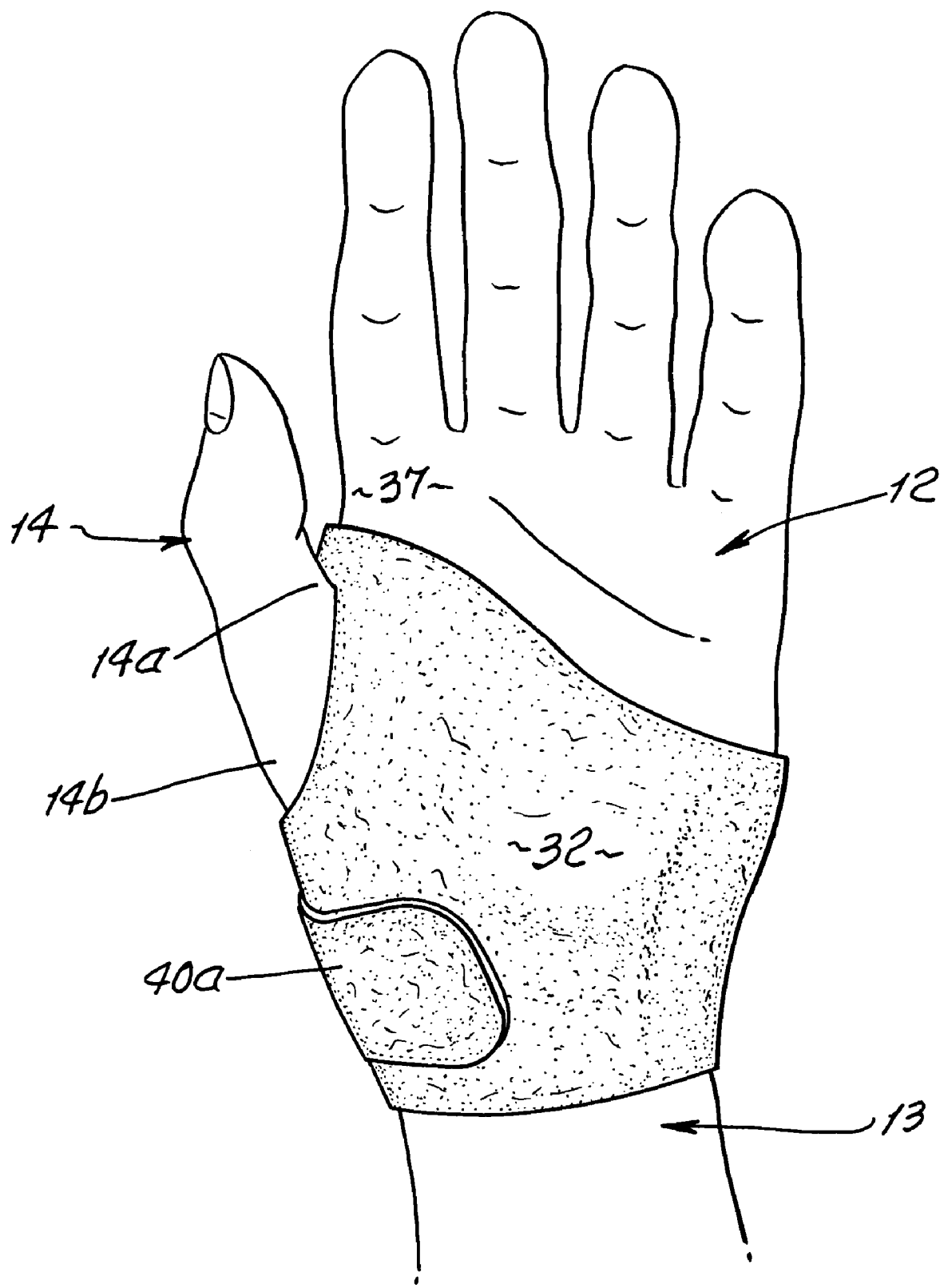
FIG. 6 is a view of said selected one brace as applied to the front side of the user's hand and wrist, and tensioned.
Figure 7:
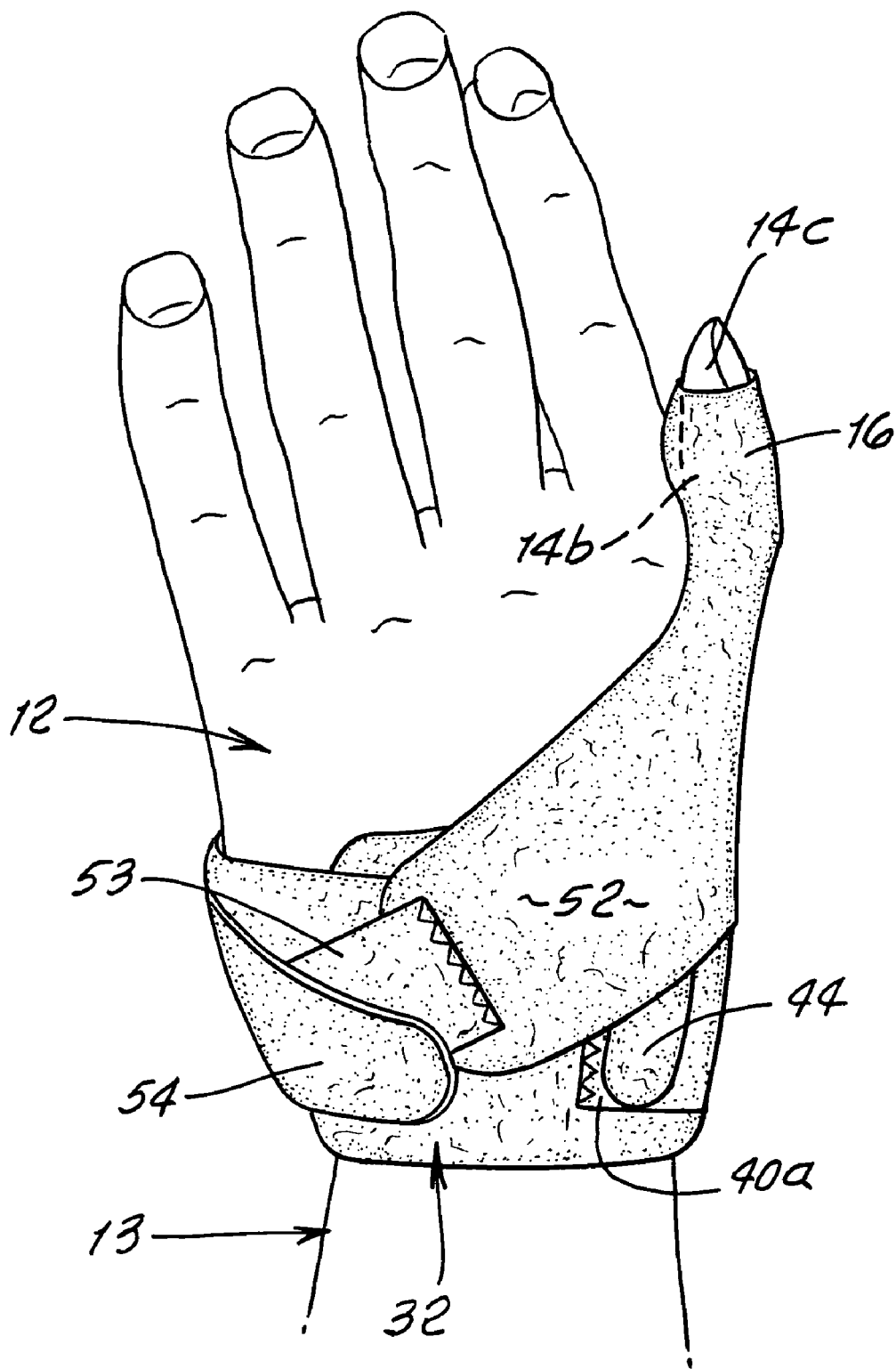
FIG. 7 is a view of the other of the braces as applied to the back side of the user's hand and wrist, and over first brace structure.
Figure 8:
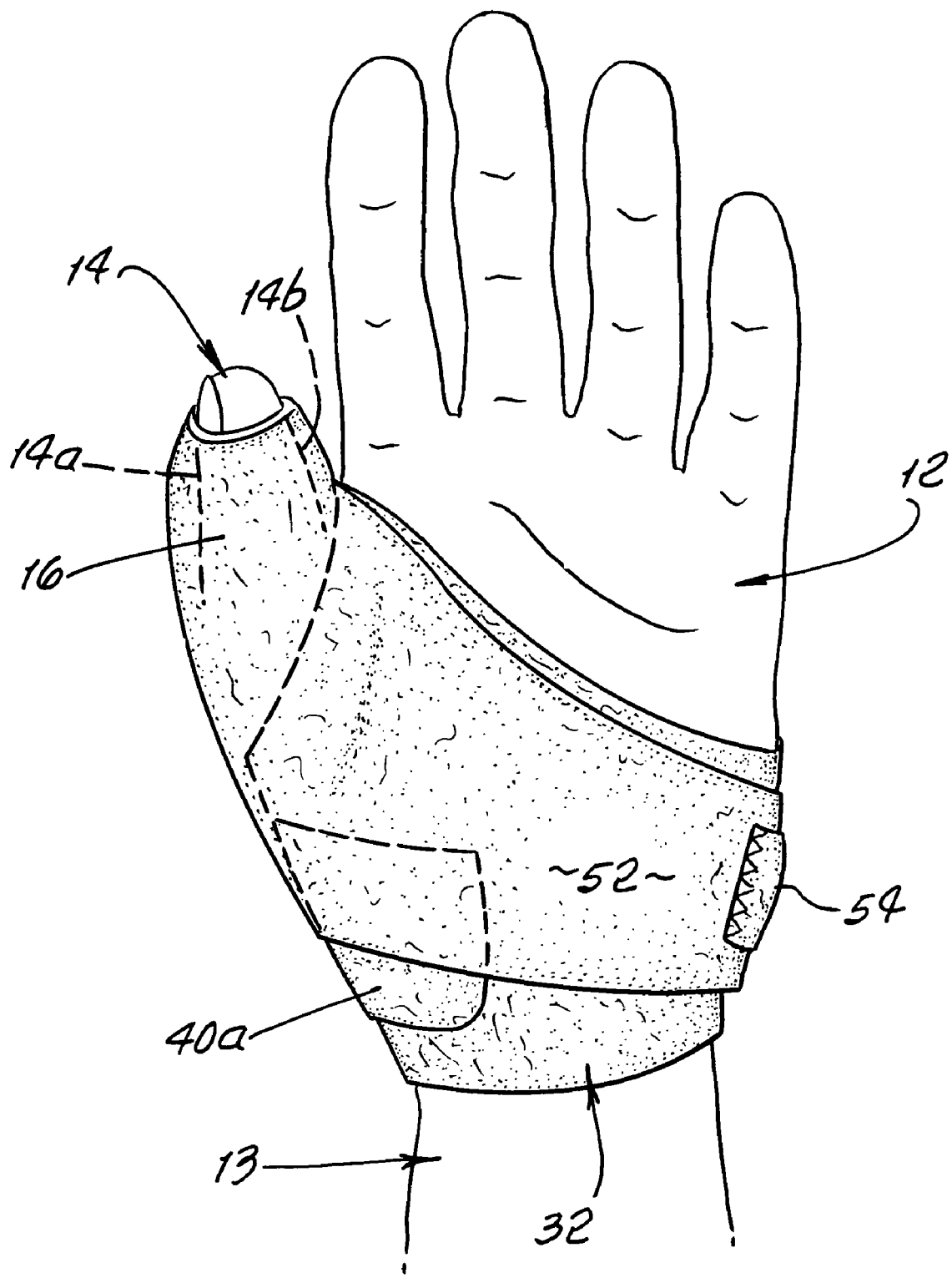
FIG. 8 is a view of said other of the braces as applied to the front side of the user's hand and wrist, and over first brace structure.

Two hand and/or wrist braces are shown and configured in FIGS. 1 and 3, at 10 and 11, in such a way that a selected brace, such as a first brace is applicable to the hand 12 and/or wrist 13 of the user (for example as seen in FIGS. 5 and 6), and also that a selected brace, such as a second brace, is applicable over at least a portion of the first brace (for example as seen in FIGS. 7 and 8). Each brace is configured for in-place retention, providing support to a substantial portion of the hand and/or wrist of the user, including lateral support of the thumb 14 at side regions 14*a* and 14*b*. Typically, when both braces are applied in position, as in FIGS. 7 and 8, the thumb receives securement forces via both braces, as for example from a tensioned strap 15 associated with one of the braces, and a sleeve 16 associated with the other of the braces. Typically, the braces are configured such that each is individually adjustable in tension, whereby dual adjustment forces are transmitted to the thumb, for enhanced securement. Such a strap as indicated at 15 on one brace, and such a thumb receiving sleeve as indicated at 16, on the other brace, are individually tensionable. The braces are made of flexible webbing material known in the medical device industry, and such material is resiliently stretchable or tensionable.

Referring to FIGS. 1 and 2, brace 10 has legs 30 and 31 that define wrap 32 extensible about the wrist of the user as seen in FIGS. 5 and 6. The legs merge at 34 with strap 15, which in use is tensioned lengthwise (see arrow), over the web region between the user's thumb 14 and forefinger 37. The strap is pulled down (see arrow) in FIG. 5 and secured, in tension, to the wrist wrap 32. For that purpose, the tab end portion 44 of the strap may carry hook or pile material at its underside as at 39, connectible to hook or pile material 40 as on a tab 40*a* attached to leg 31. When the legs are secured together to form a wrist wrap, tab 40 connects to leg 30, as via hook and pile connection.

Also, tab 42 on leg 30 is secured to leg 31, as via press together of hook or pile material 43 on 42 and hook or pile material on the underside of leg 31. Since the interconnected legs form an anchoring wrap, about the wrist, the tensioned strap 15 remains in tension as it is end connected at 39 with the outer surface 40 of 40*a*. This provides securement for the thumb and the CMC joint of the user's hand, below the thumb.

Figure 4:
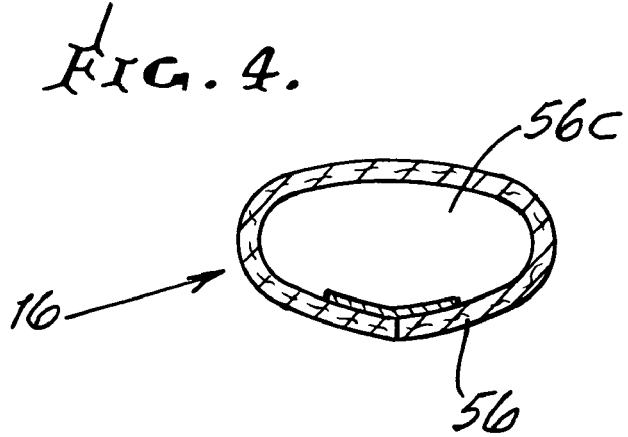
FIG. 4 is a section taken on lines 4-4 of FIG. 3.

Referring to FIGS. 3 and 4, and also FIGS. 7 and 8, brace 11 has legs 50 and 51 that when applied to the wrist define a wrap 52 extensible about the wrist of the user, as seen in FIGS. 7 and 8. Also, in those views, the wrap 52 extends over and about the wrap 32, compressing the latter, as the legs 50 and 51 are tensioned and interconnected via hook and pile tabs 53 and 54. See FIG. 3. Legs 50 and 51 merge at region 55 below a sleeve 16 applicable over the user's thumb, and subjected to tension by the anchoring wrap 52. Sleeve 16 typically tapers upwardly as shown, directionally toward the outer extent 14c of the thumb, in FIG. 8. Note in FIG. 3 the sleeve concave lower edge 56a, with edge sections 56a' and 56a" adapted to conform to the hand inner and outer surfaces below and proximate the web region between the thumb and forefinger. Thus, the two braces cooperate in this region, via the strap and sleeve, to very firmly secure the thumb in position, the sleeve extent 56c above that region being consequently securely positioned to establish added thumb position securement.

The thumb entrance region to the sleeve interior is designated at 58 in FIG. 3, that region extending to the merging region 56a''' of the edge extents 56a' and 56a". Accordingly, the sleeve is anchored in position by the wrap 52, connected over the wrap 32, whereby the wraps 32 and 52 may together add to sleeve and thumb position securement, as seen in FIGS. 7 and 8.

It will be understood that the brace 10 may be applied first to the hand, and brace 11 applied over brace 10, which may provide more comfort to the user, while retaining the advantages of dual brace secure positioning of the thumb. As previously stated, each of the two braces may be used alone to provide secure positioning of the thumb, which may be adequate and/or desirable in certain cases.

Both braces 10 and 11 may be provided in a kit or package, enabling selective use, individually or in combination, as described.

We claim:

1. Hand and/or wrist support apparatus, comprising in combination,
   a) a first brace configured for application to the hand and/or wrist of the user,
   b) and a second brace configured for application over at least a portion of the first brace,
   c) each brace configured for in-place retention, providing support to a substantial portion of the hand and/or wrist of the user, including the thumb,
   d) each brace consisting essentially of flexible material, which is resiliently stretchable,
   e) each of the braces defining two legs extending outwardly and generally oppositely from a central region when the legs are extended in generally planar flattened condition.

2. The combination of claim 1 wherein the second brace is also configured for application to the hand and/or wrist of the user, the first brace configured for application over at least a portion of the second brace, providing surface contact of brace flexible materials.

3. The combination of claim 1 wherein the first brace has a first anchor portion configured for application to the wrist of the user, and the second brace has a second anchor portion configured for application over said first anchor portion.

4. The combination of claim 3 wherein the first anchor portion is a first wrap applicable to the wrist of the user, and the second anchor portion is a second wrap applicable to and over at least a portion of the first wrap.

5. The combination of claim 1 wherein the first brace includes a strap extensible over a portion of hand between the user's thumb and forefinger.

6. The combination of claim 1 wherein the second brace includes a sleeve configured to fit over and extend about the user's thumb.

7. The combination of claim 5 wherein the second brace includes a sleeve configured to fit over and extend about the user's thumb.

8. The combination of claim 1 wherein the second brace fits directly over at least said portion of the first brace, in compressive engagement therewith.

9. The combination of claim 4 wherein the second wrap fits directly over at least said portion of the first wrap, in compressive engagement therewith.

10. The combination of claim 4 including first hook and pile tabs retaining legs of the first wrap in overlapping retentive relation, and second hook and pile tabs retaining legs of the second wrap in overlapping retentive relation.

11. The combination of claim 9 wherein the first brace includes a strap extensible over a portion of hand between the user's thumb and forefinger; and the second brace includes a sleeve configured to fit over the user's thumb; and wherein the wraps retain the strap and sleeve in thumb supporting relation.

12. The combination of claim 1 wherein only one of said first and second braces is selected for application to and is applied to the hand or wrist of the user.

13. The method of use of a first and second brace as defined in claim 1 that includes,
   (f) selecting one of said first and second braces for application to the hand and/or wrist of the user, and
   (g) then applying said one of the braces to the hand and/or wrist of the user.

14. The combination of claim 12, wherein only one of said first and second brace includes a strap extensible over a portion of hand between the user's thumb and forefinger.

15. The method of claim 13 wherein only one of said first and second brace includes a strap extensible over a portion of hand between the user's thumb and forefinger, and tensioning said strap during application of only one of said first and second brace to the hand and/or wrist of the user.

16. The method of claim 15 which includes,
   (h) selecting the other of said first and second braces for application to the hand and/or wrist of user,
   (i) and then applying said other brace to the hand and/or wrist of the user,
   (j) whereby the user's thumb receives positioning support from each of said applied braces.

17. Hand and/or wrist support apparatus comprising in combination of the following two braces:
   a) a first brace configured for application to the hand and/or wrist of the user,
   b) and a second brace configured for application over at least a portion of the first brace,
   c) each brace configured for in-place retention, providing support to a substantial portion of the hand and/or wrist of the user, including the thumb,
   d) the first brace including a strap to be tensioned over a portion of hand between the user's thumb and forefinger,
   e) the second brace including a sleeve to fit over the user's thumb,
   f) each brace including a wrap that anchors the brace about the user's wrist,
   g) each brace consisting essentially of flexible material, which is resiliently stretchable.

* * * * *